United States Patent
Tsukada (10) Patent No.: US 8,283,704 B2
(45) Date of Patent: Oct. 9, 2012

(54) GAS SENSOR

(75) Inventor: Keiji Tsukada, Okayama (JP)

(73) Assignee: National University Corporation Okayama University, Okayama (JP)

( * ) Notice: Subject to any disclaimer, the term of this patent is extended or adjusted under 35 U.S.C. 154(b) by 35 days.

(21) Appl. No.: 13/063,600

(22) PCT Filed: Jun. 30, 2009

(86) PCT No.: PCT/JP2009/061912
§ 371 (c)(1),
(2), (4) Date: Mar. 11, 2011

(87) PCT Pub. No.: WO2010/029805
PCT Pub. Date: Mar. 18, 2010

(65) Prior Publication Data
US 2011/0169057 A1   Jul. 14, 2011

(30) Foreign Application Priority Data
Sep. 12, 2008 (JP) .................. 2008-235414

(51) Int. Cl.
*G01N 27/403* (2006.01)
(52) U.S. Cl. .................. 257/253; 257/E27.06
(58) Field of Classification Search .................. 257/253, 257/E27.06
See application file for complete search history.

(56) References Cited

FOREIGN PATENT DOCUMENTS

| JP | 62-237347 | 10/1987 |
|---|---|---|
| JP | 63-171351 | 7/1988 |
| JP | 01-127943 | 5/1989 |
| JP | 01-203955 | 8/1989 |
| JP | 2008-145128 | 6/2008 |
| WO | WO2005/080957 A1 | 9/2005 |
| WO | WO2005/103667 A1 | 11/2005 |
| WO | WO2008/007716 A1 | 1/2008 |

OTHER PUBLICATIONS

K. Tsukada et al., "A Proton Pumping Gate Field-Effect Transistor for a Hydrogen Gas Sensor." I.E.E.E. Sensors Journal, vol. 7, No. 9 (Sep. 2007), pp. 1268-1269 (2 pages).

T. Yamaguchi et al., "Analysis of response mechanism of a proton-pumping gate FET hydrogen gas sensor in air." Sensors and Actuators B: Chemical, 133 (2008), pp. 538-542 (5 pages).

M. Takisawa et al., "Gate Impedance Transition of Proton Pumping Gate Hydrogen Sensor in Various Gas Atmospheres." The National Conference Electrical Engineers of Japan, 2008 (1 page).

(Continued)

*Primary Examiner* — Lynne Gurley
*Assistant Examiner* — Hsin-Yi Hsieh
(74) *Attorney, Agent, or Firm* — Sterne, Kessler, Goldstein & Fox P.L.L.C.

(57) ABSTRACT

A gas sensor (30) includes two field-effect transistors and gate electrodes on gate insulation films (24) of the two field-effect transistors to detect gas using the gate electrodes. The gas sensor (30) includes a first gate electrode (5), a second gate electrode (6), and voltage applying means. The first gate electrode (5) is provided on one of the field-effect transistors. The second gate electrode (6) is provided on another one of the field-effect transistors. The voltage applying means is for, with the first gate electrode (5) and the second gate electrode (6) coupled to one another by wiring, applying thereto one of a direct-current voltage and an alternating-current voltage having a same potential or a constant voltage difference. The first gate electrode (5) and the second gate electrode (6) are made of different metals. The one field-effect transistor and the other field-effect transistor have approximately the same structures.

2 Claims, 6 Drawing Sheets

OTHER PUBLICATIONS

J. Lundstrom et al., "Catalytic Metals and Field-effect Devices—a Useful Combination." Sensors and Actuators, B vol. 1 (1990), pp. 15-20 (6 pages).

K. Tsukada et al., "A study of fast response characteristics for hydrogen sensing with platinum FET sensor." Sensors and Actuators, B vol. 114 (2006), pp. 158-163 (6 pages).

M. Takisawa et al. "Gate Impedance Transition of Proton Pumping Gate Hydrogen Sensor in Various Gas Atmospheres." National Convention Record I.E.E.E. Japan, Mar. 19, 2008, vol. 2008, No. 3, p. 229 (1 page).

English Translation of International Search Report for International Application No. PCT/JP2009/061912, Japanese Patent Office mailed Oct. 6, 2009, 2 pages.

GAS SENSOR

TECHNICAL FIELD

The present invention relates to a gas sensor to detect gas concentration.

BACKGROUND ART

A wide variety of gas sensors are known. For example, a metal oxidant ($SnO_2$) having semiconductor properties varies its resistance value when exposed to hydrogen gas due to reduction of the oxygen in the metal oxidant. Some semiconductor hydrogen sensors utilize the change in resistance value to determine gas concentration. A similar principle is used in hot-wire semiconductor hydrogen sensors, in which a metal-oxide semiconductor is fused to a platinum wire also serving as a heater and a bridge circuit detects a change in resistance value of a device. These semiconductor and hot-wire gas sensors use bulk materials that are detrimental to mass productivity and that require operating temperatures of equal to or higher than about 300° C.

Further, such electrochemical sensors are reported that have a solid electrolyte between a platinum electrode and a nickel electrode, and that measure electro motive force generated upon contact to hydrogen gas (see patent document 1).

Further, sensors using field-effect transistors are known to have high mass productivity and be operable at around room temperature. Non-patent document 1 reports a sensor using catalytic metal Pd (palladium) as a gate metal on an insulation film of a field-effect transistor.

Non-patent document 2 reports a hydrogen sensor using, similarly, Pt (platinum) as a catalytic metal.

Many conventional gas sensors have met, through long use, the problem of varied sensor output, i.e., long-term drift of sensor output. This makes it difficult to determine whether a change in sensor output is a response to gas or merely a result of drift. It is also difficult to determine whether a gas sensor is not responding because of breakdown or because, simply, there is no gas to be sensed. This necessitates periodic calibration of the gas sensor. In order to solve the problems, the inventors reported a field-effect transistor having a diagnostic function to determine whether a gas sensor is responding to gas; specifically, a proton-pumping gate FET that uses, as a gate structure, a three-layer structure of Pd, polyelectrolyte film, and Pt (see patent document 2).

[Patent Document 1] Japanese Patent Publication No. 4048444.

[Patent Document 2] Japanese Unexamined Patent Application Publication No. 2008-145128.

[Non-patent Document 1] J. Lundstrom, A. Spetz, U. Ackelid and Sundgren, "Catalytic Metals and Field-effect Devices—a Useful Combination." Sensors and Actuators, B Vol. 1(1990), pp. 15-20.

[Non-patent Document 2] K. Tsukada, T. Kiwa, T. Yamaguchi, S. Migitaka, Y. Goto, K. Yokosawa, "A study of fast response characteristics for hydrogen sensing with platinum FET sensor." Sensors and Actuators, B Vol. 114(2006), pp. 158-163.

DISCLOSURE OF THE INVENTION

Problems to be Solved by the Invention

In gas sensors, the self-diagnostic function eliminates the need for long-term maintenance and thus is in need as an essential function for widespread applications. However, the proton-pumping gate FET reported by the inventors as a gas sensor in patent document 2 necessitates patterning of the three-layer (Pd, polyelectrolyte film, and Pt) structure as a gate structure. This complicates the fabrication process.

Further, with conventional gas sensors, it is difficult to discriminate a change in sensor output caused by disturbance such as ambient electromagnetic noise and a rapid change in temperature.

Thus, there is a need for a gas sensor configuration having a self-diagnostic function with a simpler sensor structure.

In view of this, it is an object of the present invention to provide a gas sensor having a self-diagnostic function with a simplified structure.

Means of Solving the Problems

According to one aspect of the present invention, a gas sensor includes two field-effect transistors and gate electrodes provided on gate insulation films of the two field-effect transistors, and is configured to detect hydrogen gas using the gate electrodes. The gas sensor includes a first gate electrode, a second gate electrode, one voltage applying means, and a differential amplifier. The first gate electrode is provided on one of the two field-effect transistors and includes a catalytic metal that causes a dissociation response of hydrogen. The second gate electrode is provided on another one of the two field-effect transistors and includes a non-catalytic metal that does not cause a dissociation response of hydrogen. The one voltage applying means is for, with the first gate electrode and the second gate electrode coupled to one another by wiring, applying one of a direct-current voltage and an alternating-current voltage having a constant voltage difference to the first gate electrode and the second gate electrode. The one field-effect transistor and the other field-effect transistor have same structures other than materials of the gate electrodes so as to compensate for the differential between the first field-effect transistor and the second field-effect transistor measured by the differential amplifier.

In the gas sensor according to the one aspect of the present invention, a common ion conductive film may be formed on the first gate electrodes of the first field-effect transistor and the second gate electrode of the second field-effect transistor.

EFFECTS OF THE INVENTION

With the gas sensor according to the embodiments of the present invention, the gate metal materials of the two field-effect transistors are different from one another, resulting in different response properties relative to hydrogen gas. The difference in response property can be utilized to measure target hydrogen gas. Response to gas is actually possible with a conventional gas sensor using a single field-effect transistor, in which a gate metal reacts with measurement target gas to change the work function of the gate metal. However, the conventional gas sensor using a single sensor component might undergo drift of sensor output due to change in properties of the field-effect transistor over time. On the contrary, the gas sensor according to the embodiments of the present invention uses two field-effect transistors having the same structures other than the gate metal materials. At the same time, the gate electrodes of the two field-effect transistors are coupled to one another by wiring, instead of being separated, so that the one voltage applying means applies a constant voltage to the gate electrodes. This ensures same operating conditions for the two field-effect transistors constituting the gas sensor. Thus, even though the gas sensor is used for a long term, the two field-effect transistors are used in the same environment. Further, since the two field-effect transistors have the same structures (sensor structures), similar changes in properties occur. Further, the two field-effect transistors commonly undergo disturbances such as electromagnetic noise and change in temperature. This ensures that the differential amplifier measures a difference between outputs of the two field-effect transistors and compensates for the differential, thereby eliminating change in output due to disturbances and change in properties.

The gas sensor according to the embodiments of the present invention includes a common ion conductive film on the gate electrodes of the two field-effect transistors so that when exposed to measurement target gas, the gate electrodes react with the gas through the ion conductive film. This stabilizes the reaction and improves gas selectivity.

DESCRIPTION OF THE REFERENCE NUMERAL

1 Si substrate
2-1 drain
2-2 drain
3-1 source
3-2 source
4-1 p-well
4-2 p-well
5 Pt gate electrode
6 Ti gate electrode
7-1 drain wiring
7-2 drain wiring
8-1 source wiring
8-2 source wiring
9-1 gate wiring
9-2 gate wiring
10 $SiO_2$ film
11 $Si_3N_4$ film
12 ion conductive film
20-1 voltage follower circuit
20-2 voltage follower circuit
21 differential amplifier
22 voltage source
23 alternating-current voltage source
24 gate insulation film
25 catalytic metal gate transistor
26 non-catalytic metal gate transistor
30 gas sensor

BEST MODE FOR CARRYING OUT THE INVENTION

Embodiments of the present invention will be described with reference to the accompanying drawings.

[Embodiment 1]

Figure 1:
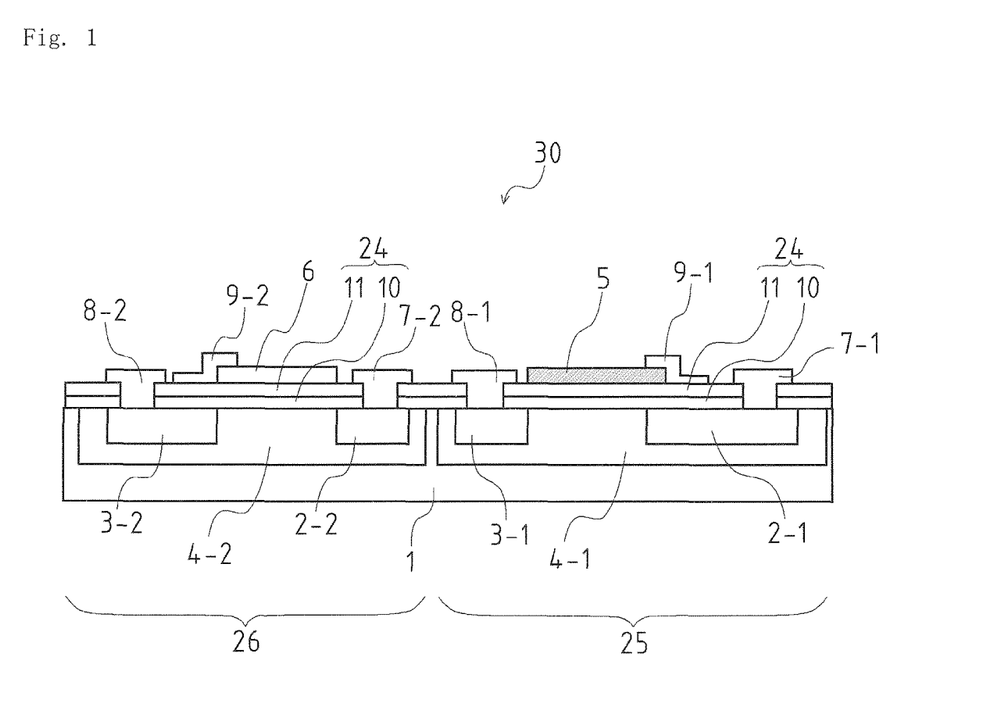
FIG. 1 is a schematic cross-sectional view of a gas sensor according to an embodiment of the present invention, illustrating a basic structure of the gas sensor.

FIG. 1 is a schematic cross-sectional view of a gas sensor according to an embodiment of the present invention, illustrating a basic structure of the gas sensor including two field-effect transistors, A gas sensor 30 illustrated in FIG. 1 is a field-effect gas sensor in which two field-effect transistors using mutually different metal materials as gate electrodes are integrated on one Si substrate 1. That is, the gas sensor 30 includes two n-type channel field-effect transistors provided on the Si substrate 1.

A catalytic metal gate field-effect transistor 25 (hereinafter referred to as catalytic metal gate transistor), which is one of the two field-effect transistors, includes a Pt gate electrode 5 formed as a first gate electrode. Using Pt (platinum), which is an example of catalytic metal, as a gate electrode material of the first gate electrode, the catalytic metal gate transistor 25 functions as a gas sensor to respond to hydrogen. Hydrogen, when exposed to Pt (platinum), dissociates into hydrogen ions (proton ions) and electrons, with the hydrogen ions then adsorbed to Pt (platinum). This causes a change in the work function of Pt (platinum). This dissociation reaction is dependent on the hydrogen concentration, and accordingly the work function also has dependency on the hydrogen concentration. A change in work function also causes a change in the operating point of a field-effect transistor, which makes the catalytic metal gate transistor 25 capable of responding to hydrogen. Further, the catalytic metal gate transistor 25 includes a p-well 4-1, which is a p-type well region, on the Si substrate 1. The p-well 4-1 includes therein a drain 2-1 and a source 3-1 with a channel formed therebetween, and a gate insulation film 24 is formed on the p-well 4-1. The gate insulation film 24 has a two-layer structure of insulation materials that are a $SiO_2$ film 10 and a $Si_3N_4$ film 11 on the $SiO_2$ film 10. The Pt gate electrode 5 is formed on the gate insulation film 24, and coupled with a gate wiring 9-1 through which to apply a constant voltage. The drain 2-1a is coupled with a drain wiring 7-1 at an upper end portion of the drain 2-1a, while the source 3-1 is coupled with a source wiring 8-1 at an upper end portion of the source 3-1.

The Pt (platinum) used as the gate electrode of the Pt gate electrode 5 causes a dissociation equilibrium reaction between the hydrogen ions and hydrogen gas, resulting in a change in work function of the platinum, Since the work function changes in relation to the hydrogen concentration, the catalytic metal gate transistor 25 including the Pt gate electrode 5 is capable of determining hydrogen concentrations.

A non-catalytic metal gate field-effect transistor 26 (hereinafter referred to as non-catalytic metal gate transistor), which is the other one of the two field-effect transistors, includes a Ti gate electrode 6 formed as a second gate electrode. Using Ti (titanium), which is an example of non-catalytic metal, as a gate electrode material of the second gate electrode, the non-catalytic metal gate transistor 26 functions as a gas sensor that shows approximately no response to hydrogen. The non-catalytic metal gate transistor 26 includes a p-well 4-2, which is a p-type well region, on the Si substrate 1. The p-well 4-2 includes therein a drain 2-2 and a source 3-2 with a channel formed therebetween, and a gate insulation film 24 is foamed on the p-well 4-2. The gate insulation film 24 has a two-layer structure of a SiO₂ film 10, which is an insulation material, and a Si₃N₄ film 11, which is another insulation material, on the SiO₂ film 10. The Ti gate electrode 6 is formed on the gate insulation film 24, and coupled with a gate wiring 9-2 through which to apply a constant voltage. The drain 2-2 is coupled with a drain wiring 7-2 at an upper end portion of the drain 2-2, while the source 3-2 is coupled with a source wiring 8-2 at an upper end portion of the source 3-2.

Since the Ti gate electrode 6 uses Ti (titanium) as its gate electrode, no dissociation equilibrium reaction occurs between the hydrogen ions and hydrogen gas, that is, no dissociation response of hydrogen occurs.

Thus, the catalytic metal gate transistor 25 and the non-catalytic metal gate transistor 26 have the same device structures except that the gate electrode materials are different from one another.

That is, the gas sensor 30 illustrated in FIG. 1 includes the catalytic metal gate transistor 25 using, as its gate electrode, catalytic metal Pt that causes a dissociation response of hydrogen and the non-catalytic metal gate transistor 26 using, as its gate electrode, Ti that does not cause a dissociation response of hydrogen. The catalytic metal gate transistor 25 and the non-catalytic metal gate transistor 26 are integrated on the Si substrate 1. The Pt gate electrode 5 and the Ti gate electrode 6 are coupled to one another by wiring to apply a constant voltage to the Pt gate electrode 5 and the Ti gate electrode 6.

Non-limiting examples of the catalytic metal include platinum, palladium, and an alloy mainly made of platinum and palladium. Non-limiting examples of the non-catalytic metal include titanium, nickel, and aluminum.

Figure 2:
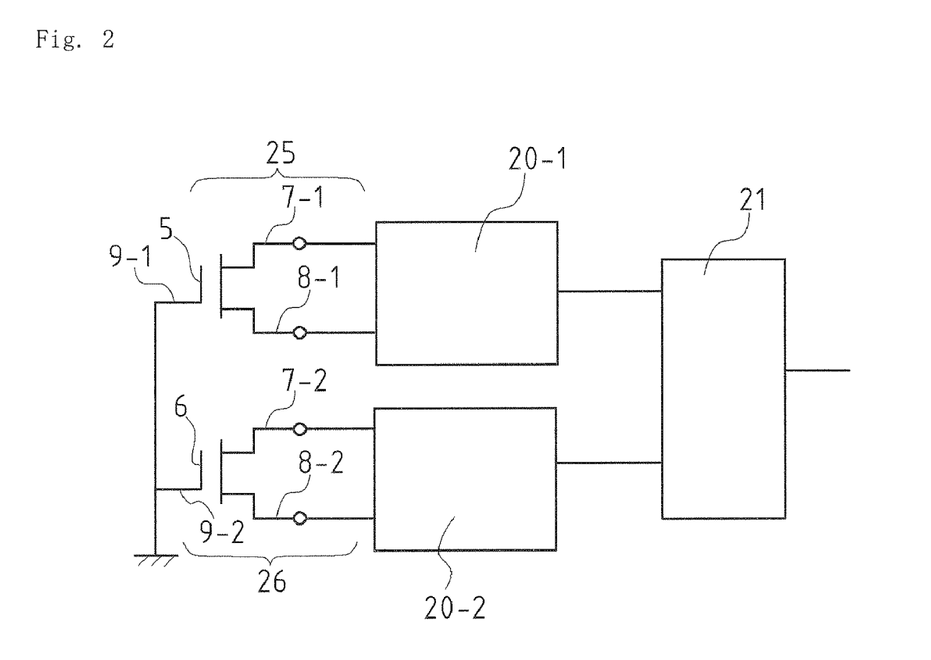
FIG. 2 is a schematic diagram illustrating a gas measuring circuit of the gas sensor.

FIG. 2 is a diagram illustrating a gas measuring circuit of the gas sensor including the two field-effect transistors illustrated in FIG. 1. As shown in FIG. 2, the gas measuring circuit of the gas sensor 30 directly couples the gate wiring 9-1 and the gate wiring 9-2, which are respectively coupled to the Pt gate electrode 5 and the Ti gate electrode 6, and grounds the gate wiring 9-1 and the gate wiring 9-2. The catalytic metal gate transistor 25 and the non-catalytic metal gate transistor 26, which respectively include the Pt gate electrode 5 and the Ti gate electrode 6, are respectively coupled to a voltage follower circuit 20-1 and a voltage follower circuit 20-2. The voltage follower circuit 20-1 and the voltage follower circuit 20-2 are generally used in gas measuring circuits using field-effect transistors to make the drain-to-source voltage and current constant and to output the voltage of the source, Further, the voltage follower circuit 20-1 and the voltage follower circuit 20-2 are coupled to a single differential amplifier 21 so that outputs of the voltage follower circuit 20-1 and the voltage follower circuit 20-2 are input to the differential amplifier 21. This enables the differential amplifier 21 to obtain a difference (a differential output) between the outputs of the catalytic metal gate transistor 25 and the non-catalytic metal gate transistor 26. With such a circuit configuration, while the catalytic metal gate transistor 25 senses a hydrogen gas, the non-catalytic metal gate transistor 26 obtains a baseline on which the hydrogen gas concentration is zero. This enables the gas sensor 30, which includes the two field-effect transistors, to compensate for the possibility of inaccuracy of the hydrogen gas concentration to be sensed, even though the gas sensor 30 meets with long-term drift, a temperature change, ambient electromagnetic noise, or another disturbance. The current-voltage properties of field-effect transistors vary depending on temperature, since temperature coefficients exist in, for example, carrier mobility. However, in the configuration of the present embodiment, two field-effect transistors having approximately the same device structures are provided to obtain a differential between the two field-effect transistors. This ensures that the differential output is a constant voltage output, which is not influenced by change in temperature, even though the current-voltage property changes due to change in temperature. Similarly, regarding the influence of ambient electromagnetic noise, since the two field-effect transistors are disposed adjacent to one another, ambient electromagnetic noise comes into the two field-effect transistors simultaneously and at the same volume. Therefore, obtaining a differential completely cancels the ambient electromagnetic noise. In the conventional method using a single field-effect transistor, a disturbance directly appears as a change in output, which makes it impossible to determine whether the change in output is actually a response to hydrogen, a result of long-term drift, or an influence of a change in temperature, ambient electromagnetic noise, or another factor. The configuration of the present embodiment of the present invention ensures obtaining actual hydrogen responses without influence of these disturbances.

Figure 3:
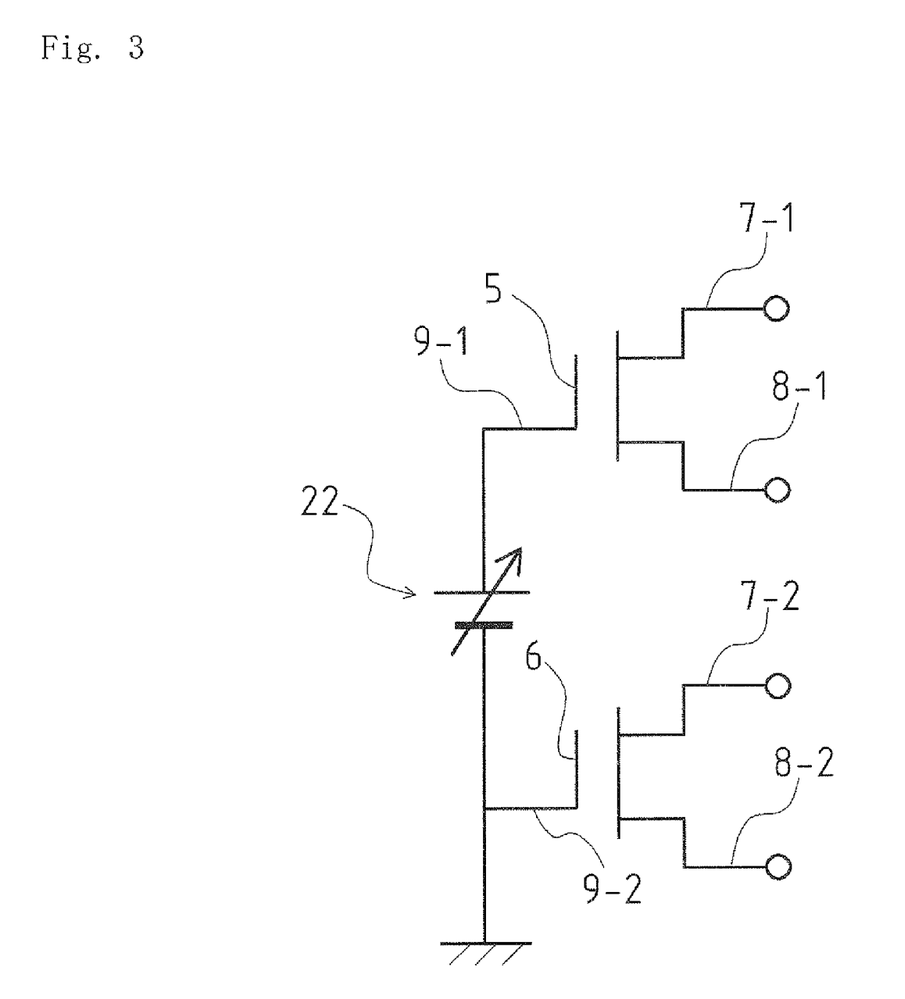
FIG. 3 is a schematic diagram illustrating a circuit configuration having a voltage source disposed along the gate wiring of the gas measuring circuit in FIG. 1

FIG. 3 is a diagram illustrating a voltage source 22 serving as voltage applying means to apply a constant voltage difference between the gate electrodes of the gas measuring circuit in FIG. 2. As described above, the catalytic metal gate transistor 25 and the non-catalytic metal gate transistor 26, which are the two field-effect transistors of the gas sensor 30, have approximately the same device structures and thus have the same electrical characteristics. However, because of the only difference between the two transistors, which is, specifically, the gate metal materials constituting the respective gate electrodes, the threshold voltages (Vt) of the catalytic metal gate transistor 25 and the non-catalytic metal gate transistor 26 are different from one another. In view of this, the voltage source 22 compensates for the difference in threshold voltage to ensure the same operating points of the two field-effect transistors.

Figure 4:
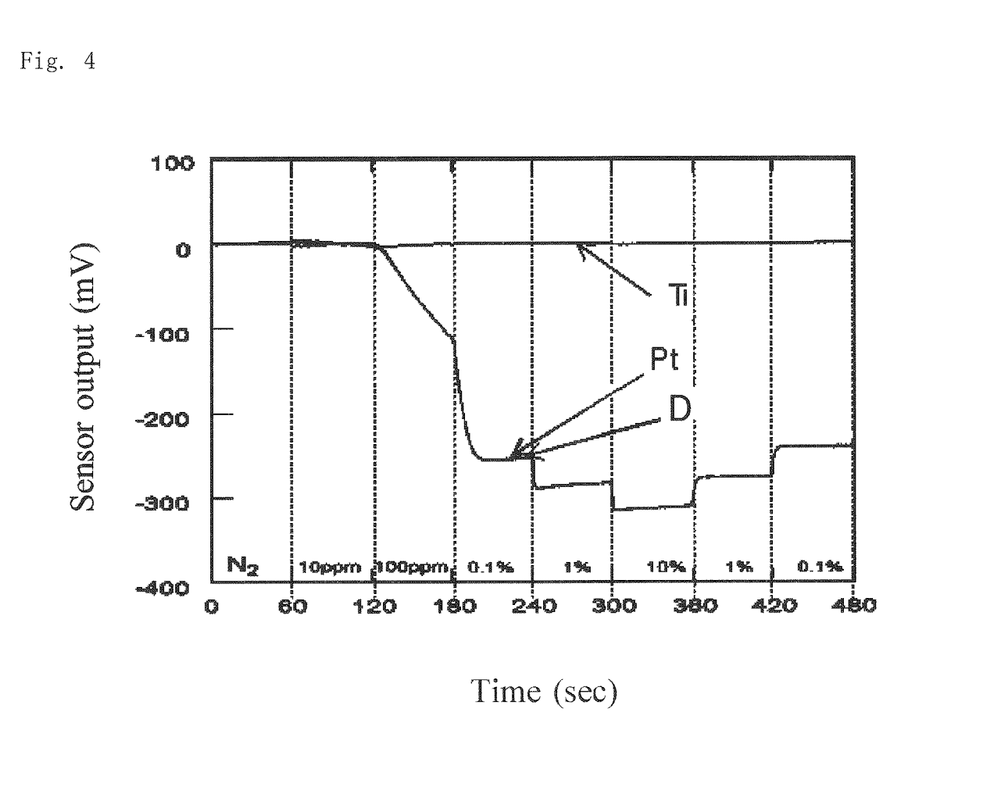
FIG. 4 is a graph showing hydrogen gas response relative to the voltage applied to the gate electrodes of the gas sensor.

FIG. 4 is a graph of hydrogen gas response relative to the voltage applied to the Pt gate electrode 5 and Ti gate electrode 6 of the gas sensor 30 having the gas measuring circuit configuration shown in FIG. 3. That is, FIG. 4 shows changes in sensor output of the gas sensor 30 relative to the hydrogen concentration. With time (second) on the horizontal axis and sensor output (mV) on the vertical axis, FIG. 4 shows results of a study for hydrogen responsivity of the gas sensor 30 obtained by allowing hydrogen gas to flow in nitrogen gas while changing the hydrogen concentration between 0% and 10% at constant time intervals (60-second intervals). Specifically, the concentration of the flowing hydrogen gas is changed on a one-digit basis (0 ppm→10 ppm→100 ppm→0.1%→1%→10%→1%→0.1%) to show the difference in sensed gas concentration that the catalytic metal gate transistor 25 and the non-catalytic metal gate transistor 26 sense as their output values (voltage values). The voltage source 22 adjusts the difference in threshold voltage (Vt) to ensure that the output of the gas sensor 30 is zero when the hydrogen is 0%. FIG. 4 shows the output of the catalytic metal gate transistor 25, which has the Pt gate electrode 5 (Pt gate output shown by the arrow Pt in FIG. 4), at the input of the differential amplifier 21; the output of the non-catalytic metal gate transistor 26, which has the Ti gate electrode 6 (Ti gate output shown by the arrow Ti in FIG. 4), at the input of the differential amplifier 21; and the output of the differential amplifier 21 as the difference between the outputs of the two transistors (output difference shown by the arrow D in FIG. 4). Specifically, the output of the catalytic metal gate transistor 25, which has the Pt gate electrode 5, corresponds to the concentration of the flowing hydrogen. Contrarily, the output of the non-catalytic metal gate transistor 26, which has the Ti gate electrode 6, remains unchanged relative to the concentration of the flowing hydrogen. Accordingly, the output of the differential amplifier 21 is approximately the same signal as the output of the catalytic metal gate transistor 25, which has the Pt gate electrode 5. In this respect, when the voltage output of the catalytic metal gate transistor 25 changes by, for example, $\Delta V1$ due to drift or some disturbance, the relationship of $\Delta V1$ with a change $\Delta V2$ in voltage output of the non-catalytic metal gate transistor 26 is $\Delta V1 = \Delta V2$ in most cases. Since the degrees of change in the voltage outputs of the two transistors are the same, the change can be compensated for when the differential amplifier 21 measures the differential (output difference). That is, the simultaneous operation of the catalytic metal gate transistor 25 and the non-catalytic metal gate transistor 26 in sensing hydrogen gas makes the two field-effect transistors commonly undergo change factors such as change in sensor properties due to temperature change and disturbance electromagnetic noise. This ensures, by obtaining the differential (output difference), cancellation of the change in the voltage output, so that the gas sensor 30 is capable of accurately measuring hydrogen gas concentration without being influenced by long-term drift and disturbance noise.

[Embodiment 2]

Figure 5:
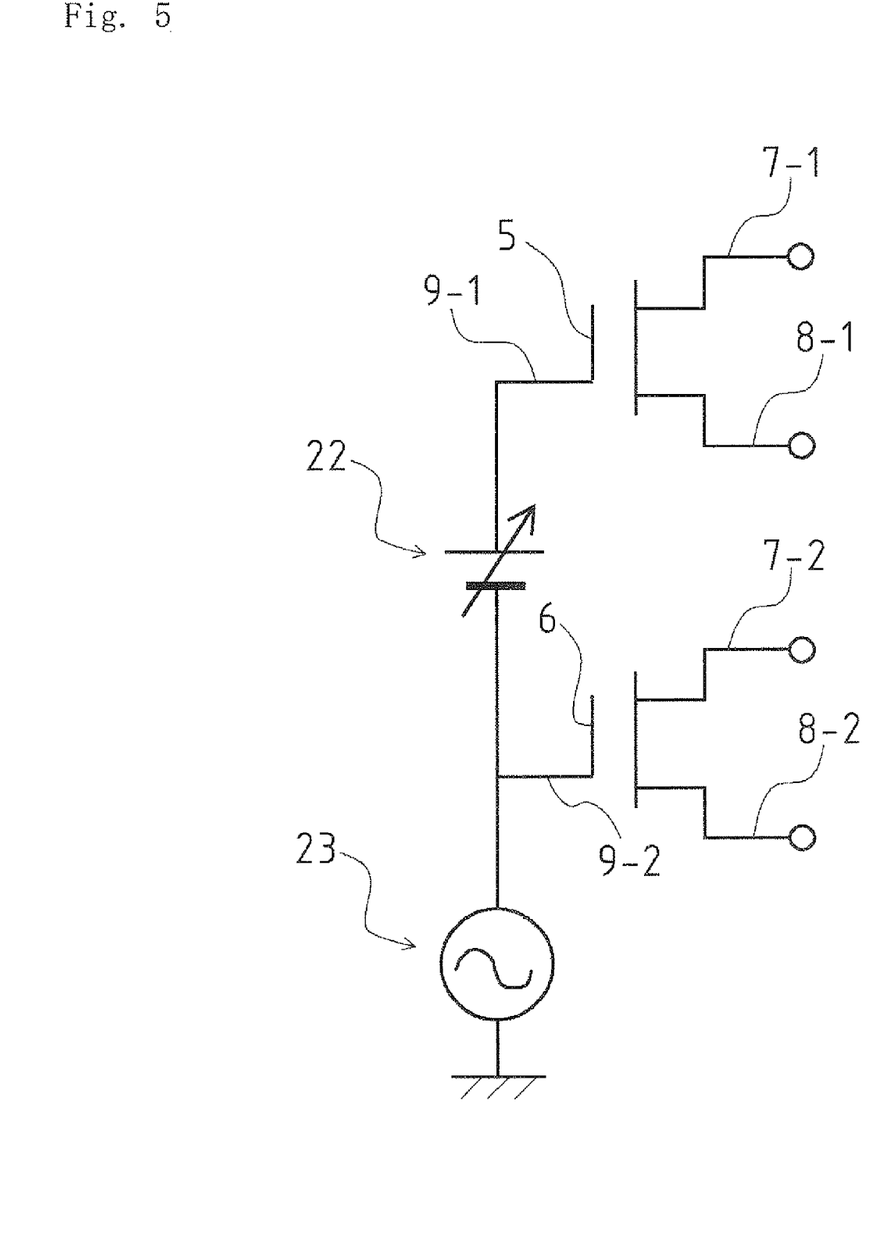
FIG. 5 is a schematic diagram illustrating a circuit configuration having a voltage source added along the gate wiring of the gas measuring circuit in FIG. 3.

FIG. 5 shows an alternating-current source 23 serving as voltage applying means added to the gas measuring circuit in FIG. 3. The alternating-current source 23 applies an alternating-current voltage $\Delta AC$ commonly to the two field-effect transistors, namely, the catalytic metal gate transistor 25 and the non-catalytic metal gate transistor 26. This signal, i.e., the alternating-current voltage $\Delta AC$, and alternating-current components $\Delta AC1$ and $\Delta AC2$ of outputs of the two field-effect transistors have the relationship $\Delta AC1 = \Delta AC2 = \Delta AC$ during normal operation of the two field-effect transistors. Therefore, the alternating-current voltage signal does not exist in the output difference of the differential amplifier 21. However, if either of the two field-effect transistors breaks down, the broken field-effect transistor shows no alternating-current voltage signal in its output or shows a different level of alternating-current voltage signal to result in $\Delta AC1 \neq \Delta AC2$. The differential amplifier 21, therefore, receives an alternating-current signal, and thus sensing the alternating-current signal ensures determination that either of the field-effect transistors is broken. In other words, a predetermined modulation signal may be input to the gate electrodes of the two field-effect transistors, namely, the Pt gate electrode 5 and the Ti gate electrode 6, to see from the differential output if the gas sensor 30 is broken.

Thus, the gas sensor 30 according to the present embodiment includes two field-effect transistors and has gate electrodes provided on the gate insulation films of the two field-effect transistors so as to detect hydrogen gas using the gate electrodes. The gas sensor 30 includes the Pt gate electrode 5 as a first gate electrode provided on the catalytic metal gate transistor 25, which is one of the two field-effect transistors and includes a catalytic metal that causes a dissociation response of hydrogen; the Ti gate electrode 6 as a second gate electrode provided on the non-catalytic metal gate transistor 26, which is another one of the two field-effect transistors and includes a non-catalytic metal that does not cause a dissociation response of hydrogen; one voltage applying means for, with the Pt gate electrode 5 and the Ti gate electrode 6 coupled to one another by wiring, applying one of a direct-current voltage and an alternating-current voltage having a constant voltage difference to the Pt gate electrode 5 and the Ti gate electrode 6; and the differential amplifier 21 configured to measure a differential between the Pt gate electrode 5 and the Ti gate electrode 6. The catalytic metal gate transistor 25, which is one of the field-effect transistors, and the non-catalytic metal gate transistor 26, which is the other one of the field-effect transistors, have the same structures other than the gate electrode materials. The differential amplifier 21 measures a difference between outputs of the two field-effect transistors and compensates for the differential. Since the gate metal materials of the two field-effect transistors are different from one another, the gate electrodes have mutually different response properties relative to hydrogen gas. The difference in response property can be utilized to measure target hydrogen gas. Response to gas is actually possible with a conventional gas sensor using a single field-effect transistor, in which a gate metal reacts with measurement target gas to change the work function of the gate metal. However, the conventional gas sensor using a single sensor component might undergo drift of sensor output due to change in properties of the field-effect transistor over time. On the contrary, the gas sensor according to the embodiments of the present invention uses two field-effect transistors having the same structures other than the gate metal materials. At the same time, the gate electrodes of the two field-effect transistors are wired to one another, instead of being separated, so that the one voltage applying means applies a constant voltage to the gate electrodes. This ensures same operating conditions for the two field-effect transistors constituting the gas sensor. That is, the one voltage applying means compensates for the difference in threshold voltage between the two field-effect transistors to ensure the same operating points of the two field-effect transistors. Thus, even though the gas sensor is used for a long term, the two field-effect transistors are used in the same environment. Further, since the two field-effect transistors have the same structures (sensor structures), similar changes in properties occur. Further, the two field-effect transistors commonly undergo disturbances such as electromagnetic noise and change in temperature. This ensures elimination of the change in output that might be caused due to a change in properties or due to disturbances, by predetermined processing after measuring the signals of the two field-effect transistors; specifically, the differential amplifier 21 measures the difference between outputs of the two field-effect transistors and compensates for the differential.

Use of a catalytic metal as the first gate electrode and a non-catalytic metal as the second gate electrode ensures selective response to measurement target hydrogen. Use of a non-catalytic metal as the gate electrode of the other one of the field-effect transistors ensures non-responsive properties relative to hydrogen. Combining the two field-effect transistors ensures a gas sensor having a diagnostic function to compensate for a long-term property change or disturbances such as change in temperature and ambient electromagnetic noise, without degrading the hydrogen response property of the field-effect transistor that uses the catalytic metal.

Further, measuring the output difference between the two field-effect transistors cancels long-term property changes that occur to the two field-effect transistors and cancels disturbances such as change in temperature and ambient electromagnetic noise.

Further, inputting a modulation signal to the two field-effect transistors and measuring the output difference between the two field-effect transistors ensure that a breakdown signal is generated when the gas sensor fails, thereby ensuring determination as to whether the gas sensor is broken down. Thus, the gas sensor itself has a self-diagnostic function.

Further, integrating the two field-effect transistors on a single Si substrate uniformizes the properties of the two field-effect transistors, thereby ensuring a diagnostic function of higher accuracy.

[Embodiment 3]

Figure 6:
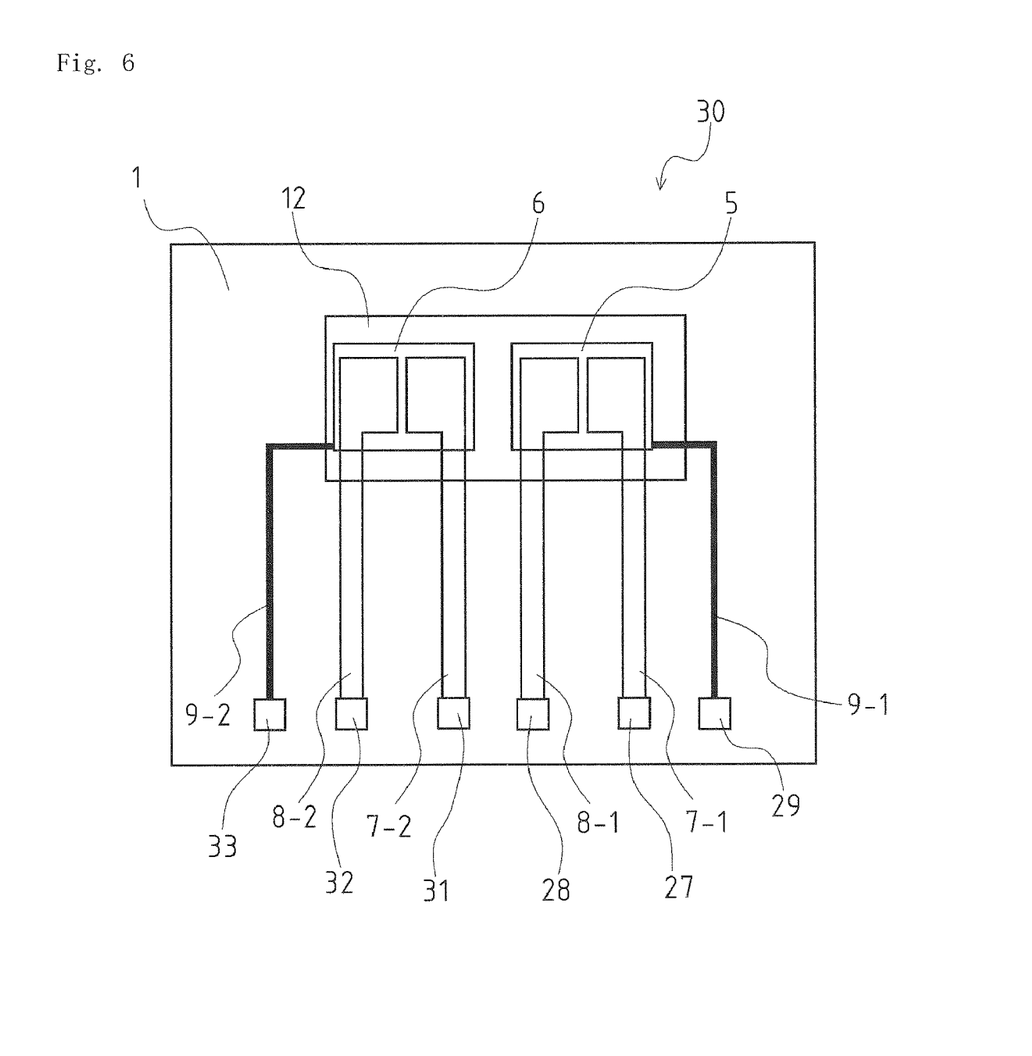
FIG. 6 is a schematic plan view of a gas sensor having a common ion conductive film formed on the gate electrodes of a first field-effect transistor and a second field-effect transistor, illustrating a basic structure of the gas sensor.

FIG. 6 is a schematic view of the gas sensor 30 including the two field effect transistors according to an embodiment of the present invention, illustrating a basic structure of a sensor chip plane having a common ion conductive film formed on the gate electrodes. In order to couple the gas sensor 30 to an external measuring circuit (not shown), a drain electrode pad 27, a source electrode pad 28, and a gate wiring electrode pad 29 of the catalytic metal gate transistor 25, and a drain electrode pad 31, a source electrode pad 32, and a gate wiring electrode pad 33 of the non-catalytic metal gate transistor 26 are provided adjacent to the chip of the gas sensor 30. The Pt gate electrode 5 and the Ti gate electrode 6 is covered with a common ion conductive film 12. The common ion conductive film 12 in the present embodiment is a perfluoro-ion-exchange film having proton conductivity. The perfluoro-ion-exchange film having proton conductivity selectively allows proton ions to permeate through the film so that the proton ions can move to the gate electrodes under the ion conductive film 12. Use of such polyelectrolyte ion conductive film 12 ensures a hydrogen gas sensor having a stabilized reaction with hydrogen gas on the gate electrodes and thus having high selectivity.

It should be noted that use of, instead of the above-described polyelectrolyte film, a film such as of a phosphoric acid electrolyte that permeates hydrogen ions therethrough also ensures a hydrogen gas sensor having high selectivity.

Thus, the gas sensor 30 according to the present embodiment has the common ion conductive film 12 formed on the Pt gate electrode 5 and the Ti gate electrode 6, which serve as the gate electrodes of the two field-effect transistors, so as to effect the reaction between gas and the electrodes through the ion conductive film 12, thereby ensuring a stabilized reaction and improved gas selectivity.

The gas sensor 30 according the embodiments of the present invention combines two field-effect transistors having sensor structures that are different from one another only in their gate metal materials, with one of the two field-effect transistors using a metal having a catalytic function relative to hydrogen to cause a hydrogen response and the other one of the two field-effect transistors using a metal without a catalytic function not to cause a hydrogen response, so as to obtain a differential between the field-effect transistors. This ensures a gas sensor 30 capable of compensating for long-term drift of its sensor components, namely the field-effect transistors, without being influenced by change in temperature, disturbance electromagnetic noise, and other environmental factors. Further, inputting a modulation signal to the gate electrodes of the two field-effect transistors ensures that a breakdown signal is generated when one of the field-effect transistors fails, thereby ensuring a self-diagnostic function of the gas sensor.

It should be understood that the present invention should not be limited to the above described examples and embodiments, and numerous modifications and variations to the above-described design are possible without departing from the technical concept of the present invention.

[Industrial Applicability]

The present invention relates to a gas sensor to measure gas concentration. The gas sensor excels in selectivity and response speed particularly for hydrogen response, and as such, is usable as hydrogen sensors. The present invention is usable as gas detectors in gas plants, hydrogen gas stations, and fuel battery systems mounted in, for example, hydrogen vehicles, home, and buildings.

The invention claimed is:

1. A gas sensor comprising:
   a first field-effect transistor having a first gate insulation film;
   a second field-effect transistor adjacent to the first field-effect transistor and having a second gate insulation film;
   a first gate electrode on the first gate insulation film and comprising a catalytic metal that causes a dissociation response of hydrogen;
   a second gate electrode on the second gate insulation film, the second gate electrode being coupled to the first gate electrode by wiring, the second gate electrode comprising a non-catalytic metal that does not cause dissociation response of hydrogen, the second gate electrode and the first gate electrode being used to detect hydrogen gas;
   a single voltage applying unit configured to apply to the first gate electrode and the second gate electrode at least one of a direct-current voltage and an alternating-current voltage having a constant voltage difference; and
   a differential amplifier configured to measure a differential between the first gate electrode and the second gate electrode,
   wherein the first field-effect transistor and the other field-effect transistor have same structures except that the first gate electrode comprises the catalytic metal and the second gate electrode comprises the non-catalytic metal, so as to compensate the differential between the first field-effect transistor and the second field-effect transistor measured by the differential amplifier.

2. The gas sensor according to claim 1, wherein a common ion conductive film is formed on the first gate electrode of the first field-effect transistor and the second gate electrode of the second field-effect transistor.

* * * * *